United States Patent
Sato

(10) Patent No.: US 7,912,268 B2
(45) Date of Patent: Mar. 22, 2011

(54) IMAGE PROCESSING DEVICE AND METHOD

(75) Inventor: Makoto Sato, Setagaya-ku (JP)

(73) Assignee: Canon Kabushiki Kaisha, Tokyo (JP)

( * ) Notice: Subject to any disclaimer, the term of this patent is extended or adjusted under 35 U.S.C. 154(b) by 598 days.

(21) Appl. No.: 11/568,020

(22) PCT Filed: Jun. 7, 2005

(86) PCT No.: PCT/JP2005/010757
§ 371 (c)(1),
(2), (4) Date: Oct. 17, 2006

(87) PCT Pub. No.: WO2005/120353
PCT Pub. Date: Dec. 22, 2005

(65) Prior Publication Data
US 2008/0292174 A1  Nov. 27, 2008

(30) Foreign Application Priority Data
Jun. 14, 2004  (JP) .................................. 2004-176083

(51) Int. Cl.
*G06K 9/00* (2006.01)
(52) U.S. Cl. .................................. 382/130; 378/98.11
(58) Field of Classification Search .................. 600/300, 600/407; 382/100, 128, 129, 130, 131, 132, 382/133, 134, 173, 151, 181, 276; 128/920; 378/1, 37, 21, 41, 42, 38, 44, 51, 62, 65, 378/146
See application file for complete search history.

(56) References Cited

U.S. PATENT DOCUMENTS

| | | | | |
|---|---|---|---|---|
| 3,894,181 | A | * | 7/1975 | Mistretta et al. ............ 378/98.11 |
| 4,941,164 | A | * | 7/1990 | Schuller et al. ................ 378/205 |
| 5,359,513 | A | * | 10/1994 | Kano et al. ..................... 382/128 |
| 5,715,451 | A | * | 2/1998 | Marlin ........................ 707/104.1 |
| 5,987,345 | A | * | 11/1999 | Engelmann et al. .......... 600/407 |
| 6,574,742 | B1 | * | 6/2003 | Jamroga et al. ................ 713/400 |
| 6,734,880 | B2 | * | 5/2004 | Chang et al. .................. 715/738 |
| 6,904,163 | B1 | * | 6/2005 | Fujimura et al. .............. 382/131 |

(Continued)

FOREIGN PATENT DOCUMENTS

JP  10-155746  6/1998

(Continued)

OTHER PUBLICATIONS

Machine translation of Makato et al. JPA 2004-147084, published May 20, 2004, submitted by applicant on IDS dated Oct. 26, 2010.*

*Primary Examiner* — Andrew W Johns
*Assistant Examiner* — Tahmina Ansari
(74) *Attorney, Agent, or Firm* — Fitzpatrick, Cella, Harper & Scinto

(57) ABSTRACT

The present invention provides an image processing device and method for effectively generating a difference image from plural images. The plural images generated by an image generation unit are first associated with radiography date and hour information and stored in a storage unit, at least one reference image and one comparison image are designated by an image designation unit from the stored images, the date and hour information of the designated reference image is compared with that of the designated comparison image by an image comparison unit, a difference process is executed by a difference processing unit based on an operation determined based on the comparison result, and the processed difference image is displayed on a display unit under the control of a display control unit.

17 Claims, 15 Drawing Sheets

U.S. PATENT DOCUMENTS

| | | | |
|---|---|---|---|
| 7,058,901 B1 * | 6/2006 | Hafey et al. | 715/792 |
| 7,576,757 B2 * | 8/2009 | Kariathungal et al. | 345/637 |
| 7,634,733 B2 * | 12/2009 | Sadikali et al. | 715/738 |
| 2002/0082484 A1 | 6/2002 | Baba et al. | 600/300 |
| 2002/0102014 A1 * | 8/2002 | Ozaki et al. | 382/132 |
| 2004/0172292 A1 | 9/2004 | Takekoshi et al. | 705/2 |
| 2005/0113961 A1 * | 5/2005 | Sabol et al. | 700/182 |
| 2005/0259116 A1 * | 11/2005 | Araoka | 345/619 |

FOREIGN PATENT DOCUMENTS

| | | |
|---|---|---|
| JP | 2001-291088 | 10/2001 |
| JP | 2002-200066 | 7/2002 |
| JP | 2004-33539 | 2/2004 |
| JP | 2004-105843 | 4/2004 |
| JP | 2004-147084 | 5/2004 |

* cited by examiner

FIG. 4A

NAME OF PATIENT ×××     PATIENT ID 12345

|   | TEST DATE  | TEST TIME | REGION | VIEW POSITION |
|---|------------|-----------|--------|---------------|
|   | 2003/05/06 | 09:18:07  | CHEST  | PA            |
|   | 2003/05/20 | 10:00:30  | CHEST  | PA            |
|   | 2003/06/03 | 13:59:12  | CHEST  | PA            |
|   | 2003/06/30 | 09:45:10  | CHEST  | PA            |
| R | 2003/07/16 | 11:30:24  | CHEST  | PA            |

REFERENCE IMAGE — B1
COMPARISON IMAGE — B2
M

FIG. 4B

NAME OF PATIENT ×××     PATIENT ID 12345

|   | TEST DATE  | TEST TIME | REGION | VIEW POSITION |
|---|------------|-----------|--------|---------------|
|   | 2003/05/06 | 09:18:07  | CHEST  | PA            |
| C | 2003/05/20 | 10:00:30  | CHEST  | PA            |
| C | 2003/06/03 | 13:59:12  | CHEST  | PA            |
| C | 2003/06/30 | 09:45:10  | CHEST  | PA            |
| R | 2003/07/16 | 11:30:24  | CHEST  | PA            |

REFERENCE IMAGE — B1
COMPARISON IMAGE — B2
M

FIG. 5A

NAME OF PATIENT ×××    PATIENT ID 12345

|   | TEST DATE | TEST TIME | REGION | VIEW POSITION |
|---|---|---|---|---|
| R | 2003/05/06 | 09:18:07 | CHEST | PA |
|   | 2003/05/20 | 10:00:30 | CHEST | PA |
|   | 2003/06/03 | 13:59:12 | CHEST | PA  M |
|   | 2003/06/30 | 09:45:10 | CHEST | PA |
|   | 2003/07/16 | 11:30:24 | CHEST | PA |

[REFERENCE IMAGE] B1    [COMPARISON IMAGE] B2

FIG. 5B

NAME OF PATIENT ×××    PATIENT ID 12345

|   | TEST DATE | TEST TIME | REGION | VIEW POSITION |
|---|---|---|---|---|
| R | 2003/05/06 | 09:18:07 | CHEST | PA |
|   | 2003/05/20 | 10:00:30 | CHEST | PA |
| C | 2003/06/03 | 13:59:12 | CHEST | PA |
| C | 2003/06/30 | 09:45:10 | CHEST | PA |
| C | 2003/07/16 | 11:30:24 | CHEST | PA  M |

[REFERENCE IMAGE] B1    [COMPARISON IMAGE] B2

FIG. 13A

NAME OF PATIENT ×××     PATIENT ID 12345

|   | TEST DATE | TEST TIME | REGION | VIEW POSITION |
|---|---|---|---|---|
|   | 2003/05/06 | 09:18:07 | CHEST | PA |
|   | 2003/05/20 | 10:00:30 | CHEST | PA |
| R | 2003/06/03 | 13:59:12 | CHEST | PA |
|   | 2003/06/30 | 09:45:10 | CHEST | PA |
|   | 2003/07/16 | 11:30:24 | CHEST | PA  M |

REFERENCE IMAGE  B1     COMPARISON IMAGE  B2

FIG. 13B

NAME OF PATIENT ×××     PATIENT ID 12345

|   | TEST DATE | TEST TIME | REGION | VIEW POSITION |
|---|---|---|---|---|
| C | 2003/05/06 | 09:18:07 | CHEST | PA |
| C | 2003/05/20 | 10:00:30 | CHEST | PA |
| R | 2003/06/03 | 13:59:12 | CHEST | PA |
| C | 2003/06/30 | 09:45:10 | CHEST | PA |
| C | 2003/07/16 | 11:30:24 | CHEST | PA  M |

REFERENCE IMAGE  B1     COMPARISON IMAGE  B2

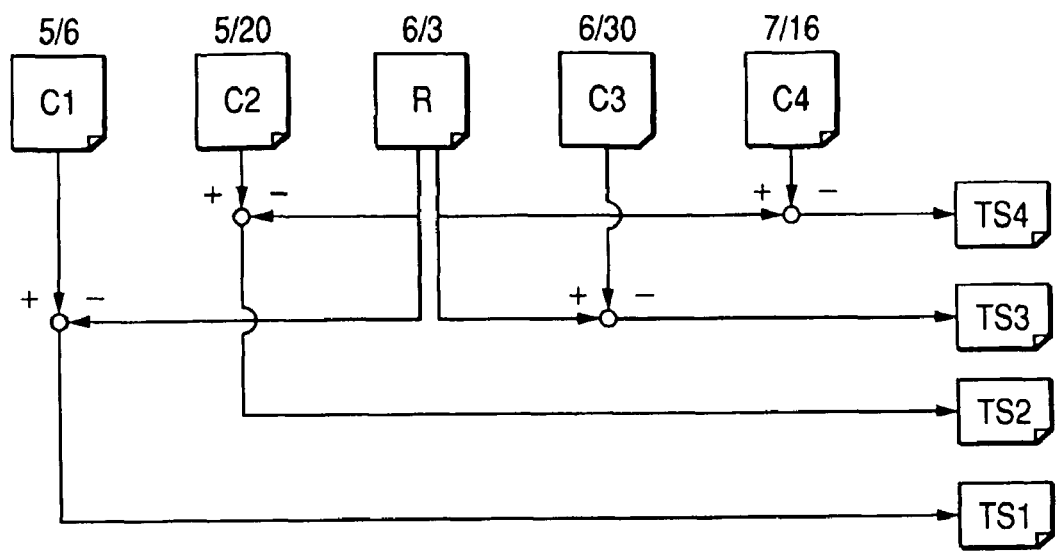
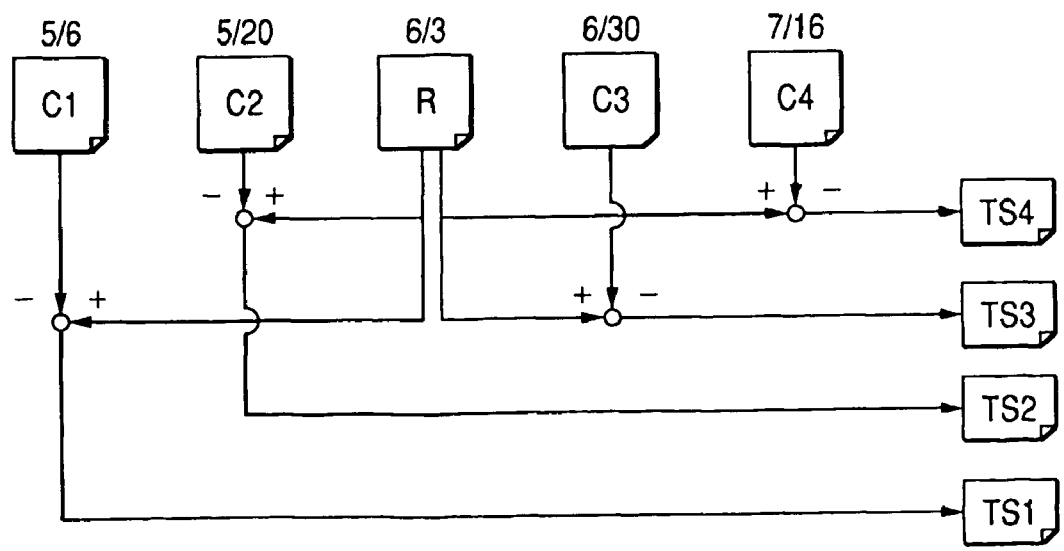

IMAGE PROCESSING DEVICE AND METHOD

TECHNICAL FIELD

The present invention relates to an image processing device and method, and more particularly, to an image processing device and method which process plural medical images.

BACKGROUND ART

In recent years, the use of digital images is advanced in the field of diagnostic imaging or medical imaging. For example, a device which radiographs or takes an X-ray image by using a semiconductor sensor has advantages as compared with a radiography system which uses conventional silver salt photography. More specifically, in such a digital radiography device, it is possible to record an image extending over a very much wider radiation exposure region, and it is also possible more easily to construct an efficient system with respect to image storing and transfer.

Moreover, by digitizing a medical image, there emerges a possibility of diagnostic form which was difficult in conventional diagnosis using silver salt photography. That is, in conventional diagnosis, in a case where plural X-ray photographs which were radiographed at different points in time during the observation of a patient's condition are compared for diagnosis, the films on which the X-ray photographs have been respectively developed are generally hung on a light box (schaukasten), and the hung films are actually compared by the diagnostician and read.

Meanwhile, in the case where the digital images are used in the diagnosis, two digital images which were radiographed at different points in time with respect to one patient are subjected to registration so that the normal anatomical structure on one digital image conforms to that of the other digital image, and then a difference process is executed on the two digital images, whereby a difference image is generated and output. Subsequently, the output difference image is compared with the pair of the two original digital images, whereby it is possible more accurately to grasp changes between the two original images.

FIG. 11 is a block diagram showing the construction of a conventional difference image generation and display device. In FIG. 11, a reference image and a comparison image which are input to a density correction unit 401 are both equivalent to medical image data of a specific region which was radiographed at different points in time. In the density correction unit 401, the image data corresponding to these images are corrected so that the distributions of the density values of the image data of these images become substantially the same. In a registration unit 402, the local relation of the anatomical structures of the specific region is acquired. Then, in a deformation unit 403, each pixel on one of these images, that is, the comparison image here, is deformed so as to overlap the corresponding pixel on the reference image, and, in a difference operation unit 404, a difference process is executed between the corresponding pixels to generate a difference image. Subsequently, the generated difference image is displayed together with the reference image and the comparison image on an image display unit 7. For example, such an operation is disclosed in Japanese Patent Application Laid-Open No. 10-155746, which corresponds to U.S. Pat. No. 5,987,345.

Here, the order of operation for the reference image and the comparison image in the above difference process is set in advance. More specifically, if it is assumed that one of these images is a past image and the other is a current image, the order of operation for these images is set to "past image"→"current image", or "current image"→"past image".

Typically, the difference image is used to extract a change which appears in the subject on the images which were radiographed at predetermined intervals in, for example, routine medical examinations. In such a use, as described above, a pair of images is used as the target, and it is only necessary to execute the difference process on each of these images in the predetermined order.

However, in a case of observing the progress of a specific patient, it is necessary to radiograph the target plural times during a relatively short period of time, sequentially observe the results of medical treatment, and further grasp the progress of the relevant medical treatment by tracing the relevant features in the sequence of images. In such conventional progress observation, there is no method of effectively generating a diachronic difference image.

DISCLOSURE OF THE INVENTION

In consideration of the above conventional situation, the present invention has an object to provide an image processing device which can execute an effective difference process in progress observation, an image processing method which is applied to the above image processing device, a program which is used to cause a computer to execute the above image processing method, and a storage medium which can store therein the above program.

To achieve the above object, the image processing device according to the present invention is characterized by comprising: a storage unit adapted to store images; an image designation unit adapted to designate a reference image and a comparison image from among the images stored by the storage unit; a comparison unit adapted to acquire radiography date and hour information of the designated reference image and the designated comparison image, and compare the radiography date and hour information of the reference image with the radiography date and hour information of the comparison image; a determination unit adapted to determine an operation in case of generating a temporal difference image based on a comparison result by the comparison unit; and a difference image generation unit adapted to generate the temporal difference image from the reference image and the comparison image by using the operation determined by the determination unit.

Moreover, the image processing method according to the present invention is characterized by comprising: an image designation step of designating a reference image and a comparison image from among plural images stored in a storage unit; a comparison step of acquiring radiography date and hour information of the designated reference image and the designated comparison image, and comparing the radiography date and hour information of the reference image with the radiography date and hour information of the comparison image; a determination step of determining an operation in case of generating a temporal difference image based on a comparison result in the comparison step; and a difference image generation step of generating the temporal difference image from the reference image and the comparison image by using the operation determined in the determination step.

BRIEF DESCRIPTION OF THE DRAWINGS

FIGS. 4A and 4B are schematic diagrams showing an example of an image selection screen according to the first embodiment of the present invention;

FIGS. 5A and 5B are schematic diagrams showing an example of the image selection screen according to the first embodiment of the present invention;

FIGS. 13A and 13B are schematic diagrams showing an example of the image selection screen according to the first embodiment of the present invention;

FIGS. 14A and 14B are diagrams for explaining the combinations of images for generating the difference image.

BEST MODE FOR CARRYING OUT THE INVENTION

Hereinafter, the embodiments to which the present invention is applied will be explained in detail with reference to the attached drawings.

First Embodiment

Construction of Image Processing Device

Figure 1:
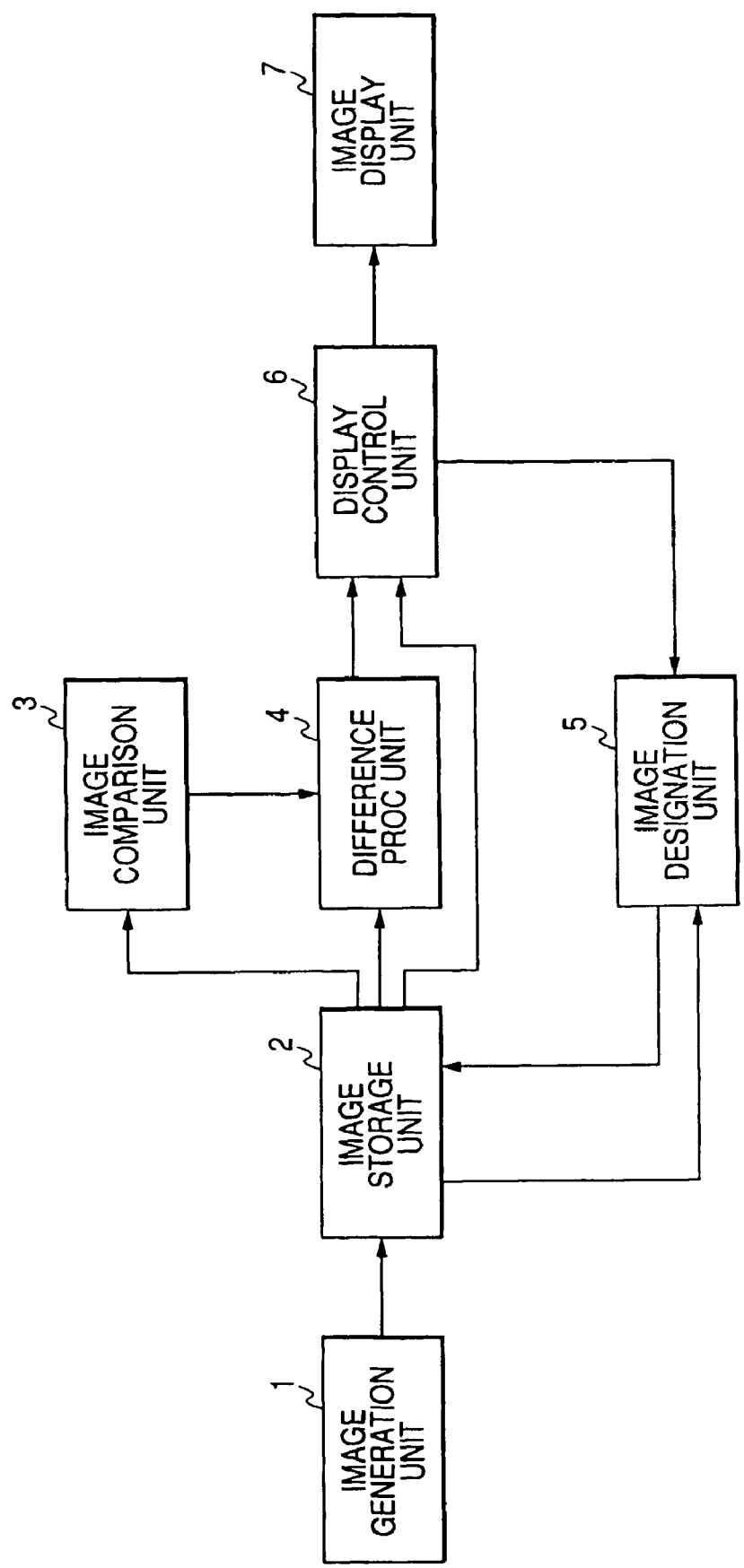
FIG. 1 is a block diagram showing the whole construction of an image processing device according to the present invention.

FIG. 1 is a block diagram showing the functional construction of the image processing device according to the first embodiment of the present invention. Initially, the whole operation of the image processing device will be schematically explained with reference to FIG. 1.

The image processing device according to the present embodiment consists of an image generation unit 1 for generating an image, an image storage unit 2 for accumulating and storing the generated images, an image designation unit 5 for designating at least one reference image and one comparison image from the images accumulated and stored in the image storage unit 2, an image comparison unit 3 for acquiring the respective radiography times of the designated reference and comparison images and specifying the context of the acquired radiography times, a difference processing unit 4 for generating a temporal difference image from the reference and comparison images based on the specified result provided by the image comparison unit 3, a display control unit 6 for controlling a display of the difference image, and an image display unit 7 for displaying the reference, comparison and difference images under the control of the display control unit 6.

In FIG. 1, the medical images generated by the image generation unit 1 are accumulated and stored in the image storage unit 2. Then, a pair or plural pairs of the stored images are read according to need, the difference process is executed on the read images by the difference processing unit 4, the difference image acquired as the result of the difference process is displayed on the image display unit 7 through the display control unit 6, and the displayed image is used in diagnosis.

Meanwhile, the former images used in the generation of the difference image are similarly displayed independently or together with the difference image on the image display unit 7 under the control of the display control unit 6, and the displayed images are then used in diagnosis.

In the above operation, the image comparison unit 3 compares the images that is the target of the difference process by the later-described method, thereby controlling the process of the difference processing unit 4. Meanwhile, the image designation unit 5 designates the images that are the target of the difference process by the later-described method, thereby determining the images to be output from the image storage unit 2 to the difference processing unit 4 based on the designation.

Figure 2:
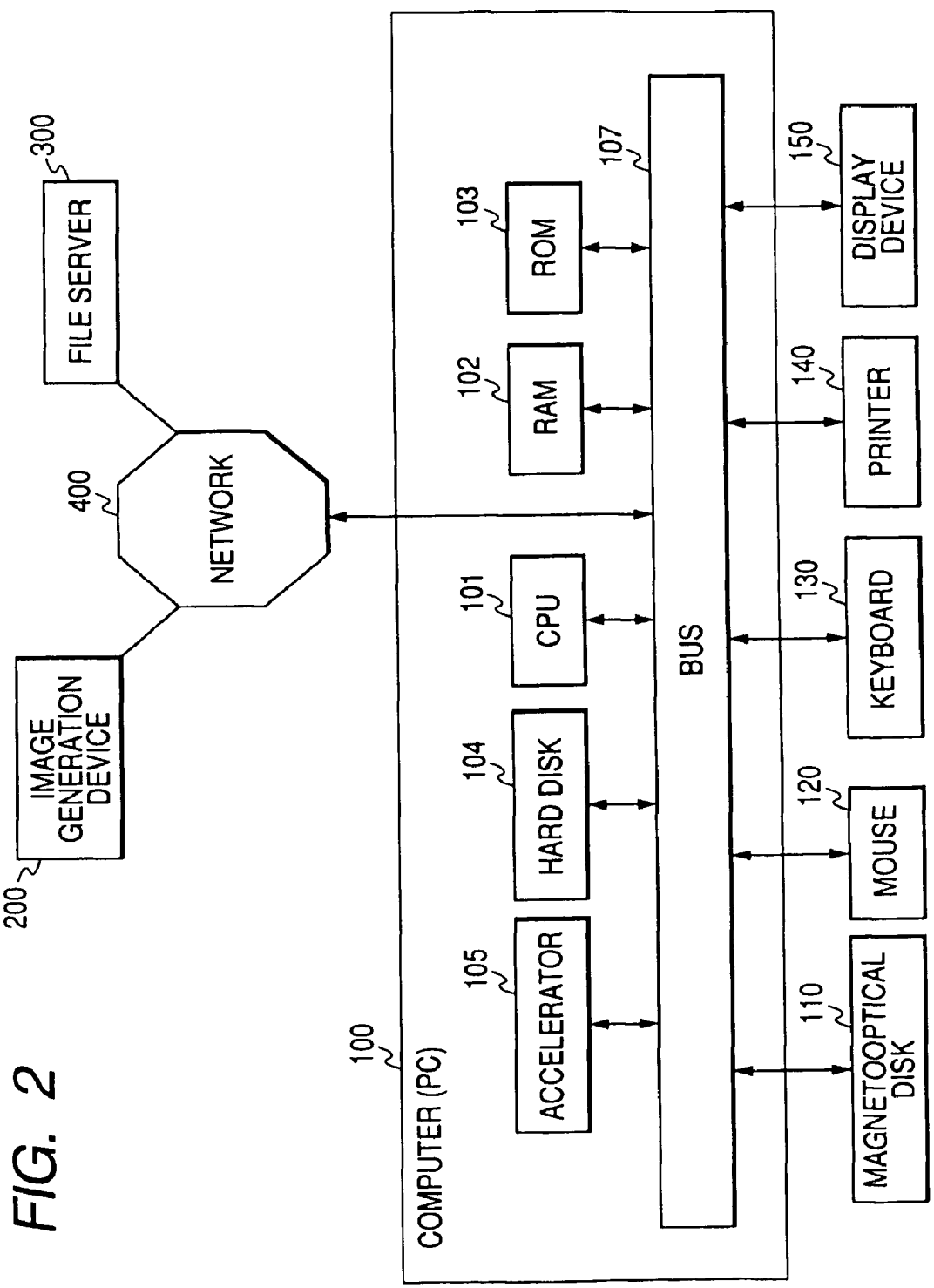
FIG. 2 is a block diagram showing the construction of a system to which the image processing device according to the present invention is applied.

For example, by achieving such functions, as shown in FIG. 2, an image generation device 200 and a file server 300 which are connected to a computer (PC) 100 through a network 400 can be used. In the drawing, various peripheral devices are connected through a bus 107 to a CPU (central processing unit) 101 which is provided in the computer 100. Moreover, the computer 100 can transmit/receive image data to/from the image generation device 200 and the file server 300 both externally connected through the network 400 through a not-shown interface. Incidentally, a magnetooptical disk 110, a mouse 120, a keyboard 130, a printer 140 and a display device 150 are connected as the peripheral devices to the computer 100, and an accelerator 105, a hard disk 104, a RAM 102 and a ROM 103 are provided as well as the CPU 101 in the computer 100.

In the above construction, the image generation unit 1 of FIG. 1 can be associated with the image generation device 200 of FIG. 2 which generates and outputs a digital image signal indicating a subject (not shown). Here, it should be noted that any types of devices capable of generating and outputting medical images may be used as the image generation unit or the image generation device. For example, an X-ray imaging device such as an FPD (Flat Panel Detector) device, a CR (Computed Radiography) device or a CT (Computed Tomography) device, an MRI (Magnetic Resonance Imaging) device, a US (Ultra Sonic) echo device, or the like may be used. In any case, the image generation unit 1 need not necessarily be limited to the above imaging (or radiography) device. That is, the image generation unit 1 may be the file server 300 of FIG. 2 which stores the images generated by a not-shown imaging device.

Moreover, in FIG. 2, the hard disk 104 of the computer 100 or the file server 300 connected to the computer 100 through the network 400 can be used as the image storage unit 2. However, the present invention is not limited to this. That is, a storage such as a hard disk built in the image generation device 200 may be used as the image storage unit.

(Image Processing Method)

Figure 3:
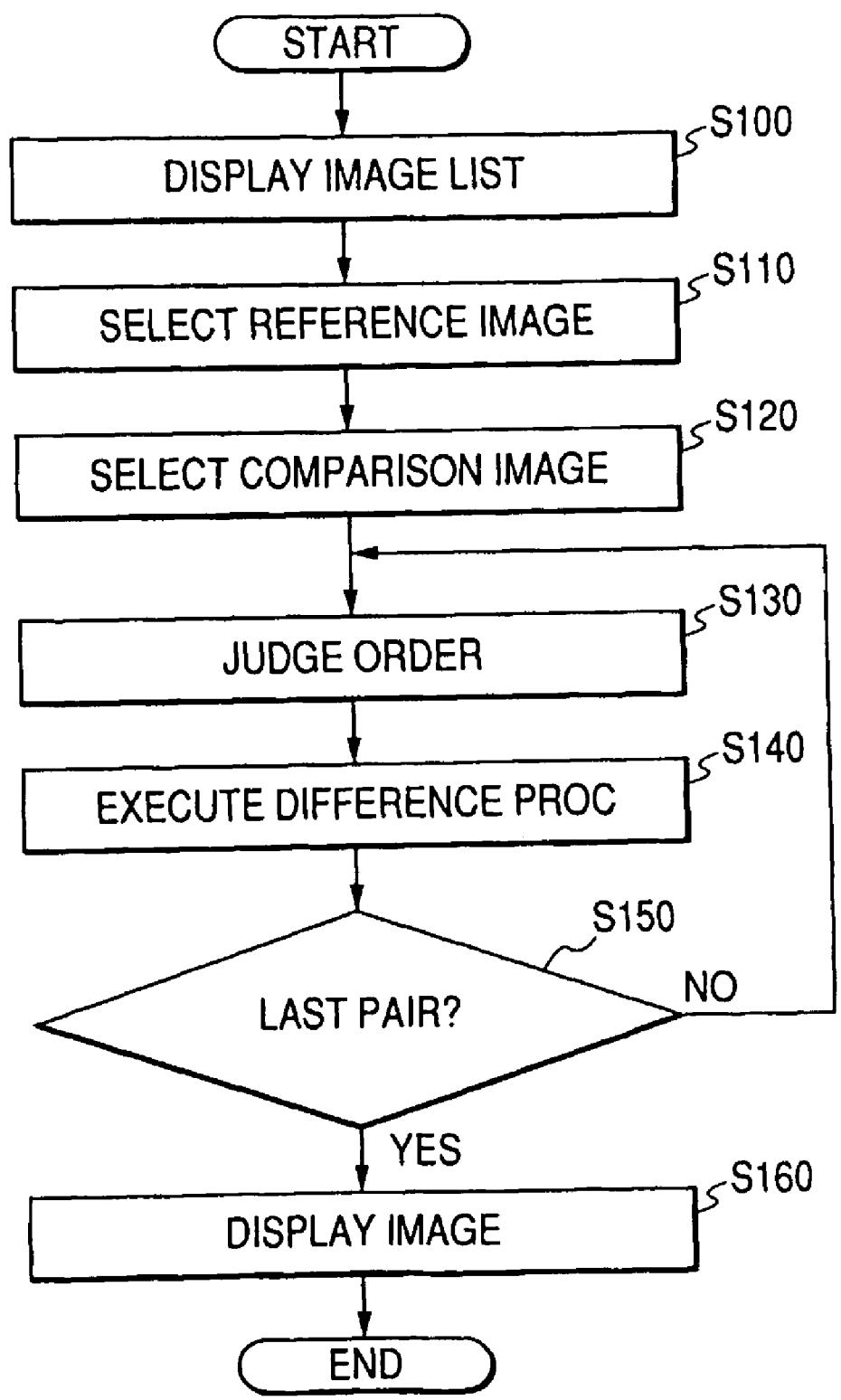
FIG. 3 is a basic flow chart of an image processing method according to the present invention.

Subsequently, the whole operation in the image processing method according to the present invention will be explained in detail with reference to the flow chart shown in FIG. 3. In the following, the explanation premises that the CPU 101 shown in FIG. 2 controls the whole processing operation and further executes the program module to achieve the relevant operation necessary for each constituent component. However, the present invention is not limited to this. That is, the present invention is applicable to various modes as described above.

(Step S100)

In response to an input by a user, the display control unit 6 reads patient information which is attached to the image of a certain specific patient being the target of radiography. Here, it should be noted that the relevant image of the patient was generated by the image generation unit 1 and stored in the image storage unit 2. Then, the display control unit 6 displays the read patient information on the image display unit 7. In the present embodiment, as shown in FIGS. 4A and 4B, dates and hours of radiography for the certain specific patient, radiography classifications (regions, line-of-vision directions, etc.) and the like are listed as the patient information. Here, the patient information may be attached to the image data stored in the image storage unit 3 or may be read from a database or the like administrated independently of the image data. In FIGS. 4A and 4B, symbol C denotes a mouse cursor, and symbols B1 and B2 denote buttons which are displayed so as to designate at least one pair of the images necessary for generating the temporal difference image and can be activated when a user shifts the mouse cursor C thereto and depresses (or clicks) it.

(Step S110)

The user first depresses the reference image button B1 to select the mode of selecting an arbitrary reference image, and then selects the line corresponding to the image to be treated as the reference image from the list displayed above the button B1. Here, in the case of actually selecting the reference image, the user only has to shift the mouse cursor C onto the intended line and then click it. FIG. 4A shows the status at that time. More specifically, FIG. 4A shows the lowest line corresponding to the latest image being selected as the reference image from the displayed list. In this connection, the mark "S" indicating that the relevant line is selected as the reference image is displayed on the left side of the selected line. At that time, the user cannot simultaneously select two or more reference images from the displayed list. Thus, even if the user attempts to select the second line corresponding to the second reference image, the previously selected line is automatically set to be unselected.

(Step S120)

The user next depresses the comparison image button B2 to select the mode of selecting an arbitrary comparison image, and then selects one or more comparison images in the same manner as for the reference image. At that time, the image designation unit 5 designates the selected image as the comparison image. In any case, the mark "R" indicating that the relevant line is selected as the comparison image is displayed on the left side of each of the selected lines. Here, although the number of selectable reference images is one, it is possible to select plural comparison images. For example, in FIG. 4B, the three images corresponding to the second to fourth lines are selected as the comparison images.

(Step S130)

The image comparison unit 3 compares the dates and hours of radiography with respect to each pair of the selected reference and comparison images, determines order of difference in the later-described difference process, and outputs the determined order to the difference processing unit 4. Incidentally, acquiring the dates and hours of radiography may be done using the information attached to the selected image data or based on information in a database stored independently of the image data.

Here, the order of difference is determined as follows. That is, based on the dates and hours of radiography of the target pair of the reference and comparison images, it is set to subtract the image of the later date and hour of radiography from the image of the earlier date and hour of radiography, or it is alternatively set to subtract the image of the earlier date and hour of radiography from the image of the later date and hour of radiography. Then, the set order is stored in the image comparison unit 3.

In the present embodiment, it is assumed to set to subtract the image of the later date and hour of radiography from the image of the past (earlier, or less recent) date and hour of radiography. However, the present invention is not limited to this. That is, the reverse order is of course acceptable.

Figure 6A:
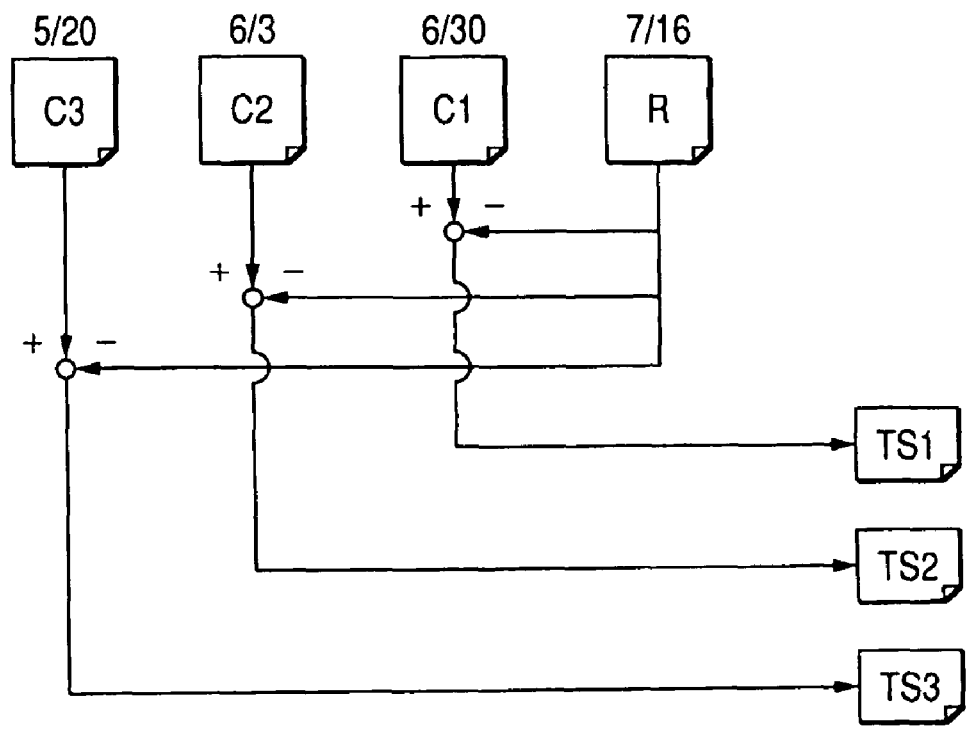
FIGS. 6A and 6B are diagrams for explaining the combinations of images for generating a difference image.

As in the present embodiment, in a case where the date and hour of radiography of the reference image is more recent than the dates and hours of radiography of the comparison images, the order of difference which is determined by the image comparison unit 3 is as shown in FIG. 6A. That is, if the reference image is given as S and the comparison images are given as R1 to R3, the difference processing unit 4 operates to generate the difference images TS1 to TS3 which satisfy the following equations:

$$TS1 = R1 - S \quad (1)$$

$$TS2 = R2 - S \quad (2)$$

$$TS3 = R3 - S \quad (3)$$

(Step S140)

Figure 11:
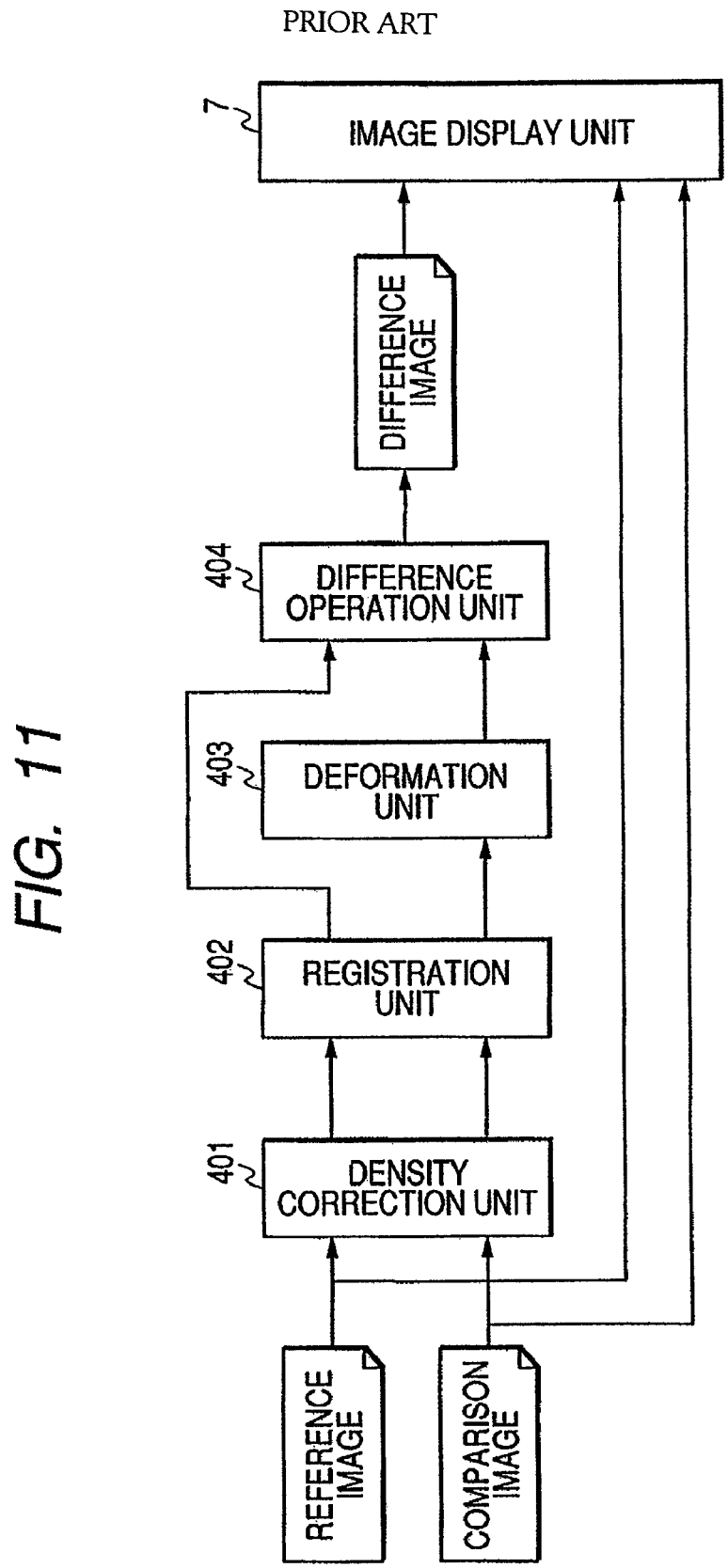
FIG. 11 is a block diagram showing the basic construction of a conventional difference process.

The difference processing unit 4 reads one pair of the reference and comparison images from the image storage unit 2, and generates and outputs the difference image through the process as suggested in FIG. 11. That is, a registration process is executed to deform the comparison image so as to conform the location of the comparison image to that of the reference image. Here, it should be noted that the reference image is not deformed, but only the comparison images are deformed. Then, the difference processing unit 4 executes the difference process (difference operation) between the reference image and the deformed comparison images. Here, it should be noted that the reference image is subtracted from each of the deformed comparison images in the order of difference operation as shown in the above equations (1) to (3) and FIG. 6A. In other words, the difference image is generated by subtracting the image of the later date and hour of radiography from the image of the earlier date and hour of radiography.

(Step S150)

The difference process is executed with respect to each pair of the reference and comparison images. Accordingly, when there are the three comparison images as shown in FIGS. 4A and 4B, it is judged whether or not the processed pair is the last pair every time each difference process ends. If it is judged that the processed pair is the last pair, the flow advances to the next step, S160. Meanwhile, if it is judged that the processed pair is not the last pair, the flow returns to the previous step, S130 to execute the difference process again.

(Step S160)

As described above, the generated three difference images are output from the display control unit 6 and then displayed on the image display unit 7, whereby the displayed difference images are used in diagnosis.

{Modification 1}

In the above, the case where the date and hour of radiography of the reference image is recent as compared with the dates and hours of radiography of the comparison images is explained. On the contrary, a case where the date and hour of radiography of the reference image is earlier than the dates and hours of radiography of the comparison images will be explained hereinafter. In the following, as well as the first embodiment, modification 1 will be explained with reference to the flow chart shown in FIG. 3.

(Step S110)

FIG. 5A shows the status that the reference image is selected. More specifically, FIG. 5A shows the status that the highest line corresponding to the earliest image is selected as the reference image from the displayed list. In this connection, the mark "S" indicating that the relevant line is selected as the reference image is displayed on the left side of the selected line.

(Step S120)

As well as in the first embodiment, the user selects the comparison image by using the mouse. At that time, the mark "R" indicating that the relevant line is selected as the comparison image is displayed on the left side of each of the selected lines. For example, in FIG. 5B, the three images corresponding to the third to fifth lines are selected as the comparison images. Here, the comparison images are all selected after the reference image is selected.

(Step S130)

The image comparison unit 3 compares the dates and hours of radiography with respect to each pair of the selected reference and comparison images, determines order of difference in the later-described difference process, and outputs the determined order to the difference processing unit 4.

Figure 6B:
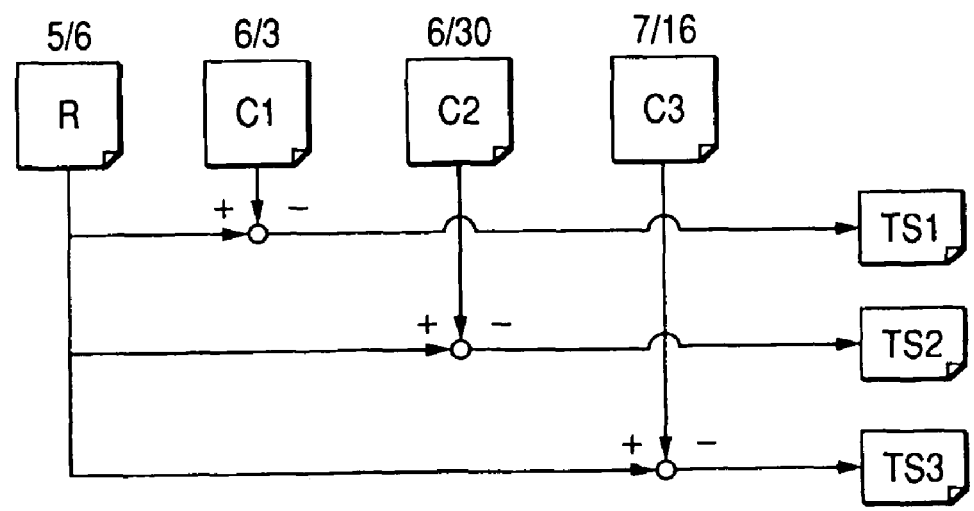

In the present embodiment, the comparison images are newly radiographed as compared with the reference image, the order of difference which is determined by the image comparison unit 3 is as shown in FIG. 6B. That is, if the reference image is given as S and the comparison images are given as R1 to R3, the difference processing unit 4 operates to generate the difference images TS1 to TS3 which satisfy the following equations:

$$TS1 = S - R1 \quad (4)$$

$$TS2 = S - R2 \quad (5)$$

$$TS3 = S - R3 \quad (6)$$

(Step S140)

As well as the above explanation, the difference processing unit 4 generates and outputs the difference image. The registration process is executed to deform the comparison image so as to conform the location of the comparison image to that of the reference image. Here, it should be noted that each of the deformed comparison images is subtracted from the reference image in the order of difference operation as shown in the above equations (4) to (6) and FIG. 6B, thereby generating the difference image.

Here, since the following steps are the same as those already explained, the explanation thereof will be omitted.

By executing the above process, it is possible to effectively generate the difference images even if there are plural combinations of the images to be compared. In addition, it is always possible to uniquely maintain the relation between a signal in the difference image and a change actually occurred between the images.

Figure 7A:
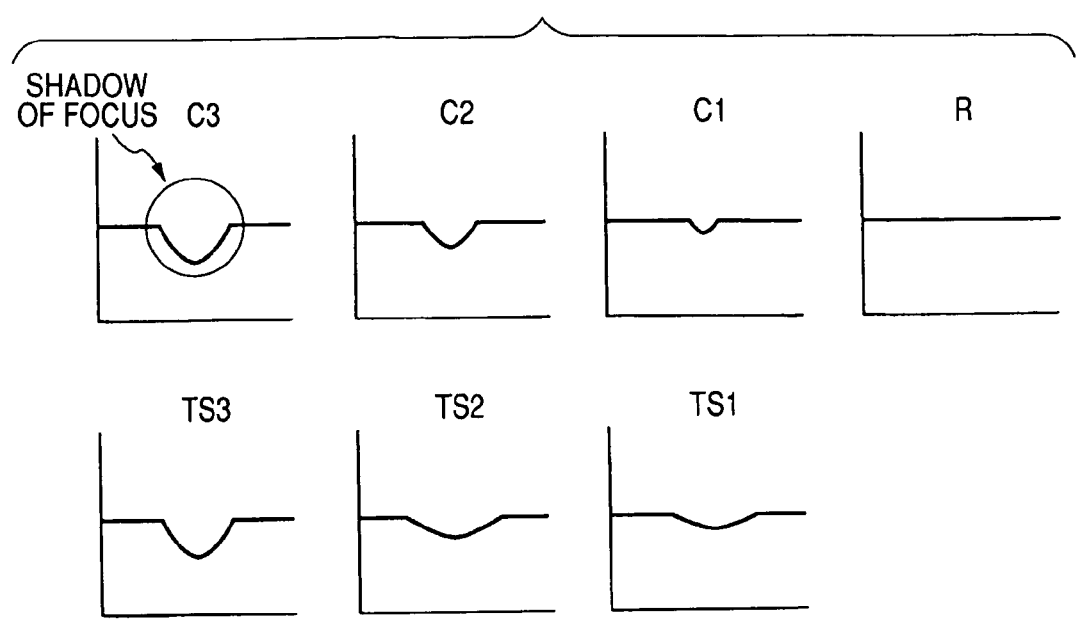
FIGS. 7A and 7B are diagrams for explaining the relation between a change of shadow and a difference signal.
Figure 7B:
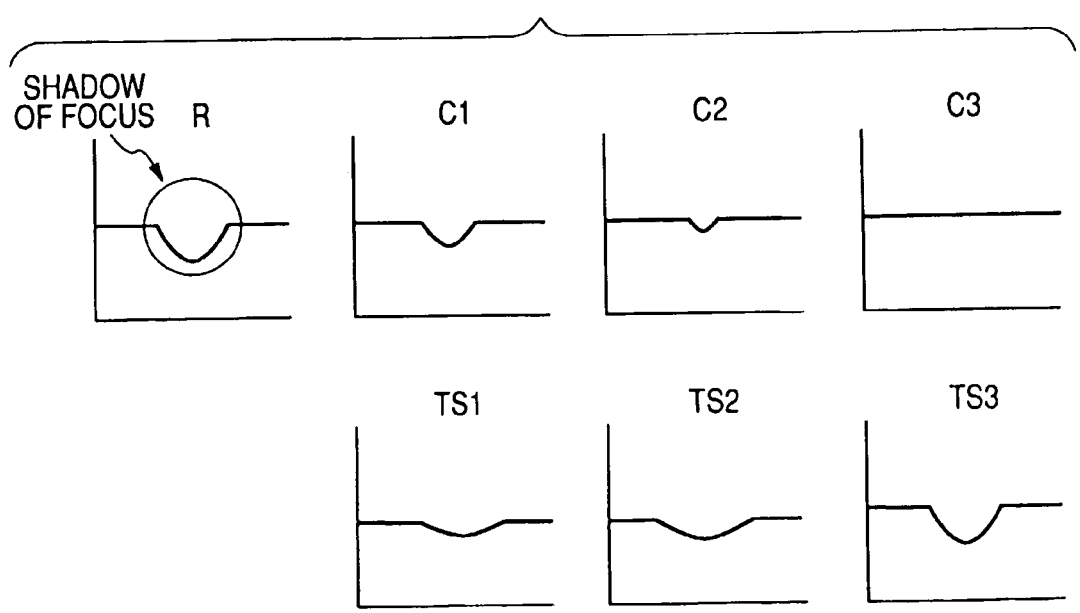

FIGS. 7A and 7B are schematic diagrams which respectively show, as one-dimensional pixel value data, examples of the images and the temporal differences in the above first embodiment and the modification 1.

First, each of the upper four plots shown in FIG. 7A indicates the pixel value in the vicinity of the shadow of focus (seat of disease) in each image, and these four plots are corresponding to FIGS. 4A and 4B and FIG. 6A. More specifically, the shadow of focus becomes small gradually from the comparison image R1 to the comparison image R3, and then the shadow of focus completely disappears in the reference image S which was most recently radiographed. Here, if the difference images TS1, TS2 and TS3 are generated as shown by FIG. 6A and equations (1) to (3), the condition of the change of the shadow is plotted as the difference signal having the low pixel value as opposed to the background portion on which any change does not occur in the difference image. The magnitude of the difference signal becomes small according as the shadow of focus becomes small. Then, in the difference between the comparison image R3 in which the shadow approximately disappears and the reference image S, the difference signal has the value substantially the same as that of the background portion.

Meanwhile, with respect to the example shown in FIGS. 5A and 5B and FIG. 6, the difference signal is acquired as shown in FIG. 7B. That is, in both the cases, the shadow of focus becomes small gradually, and the difference signal corresponding to the shadow of focus comes to have the low value with respect to the background on which any change does not occur. Incidentally, in a case of displaying the above difference signal, for example, the signal value corresponding to the background portion is set to be equivalent to the median of the brightness level capable of being displayed by a display device such as a CRT monitor or the like, and the display itself is executed by using, e.g., a gray region.

Figure 8A:
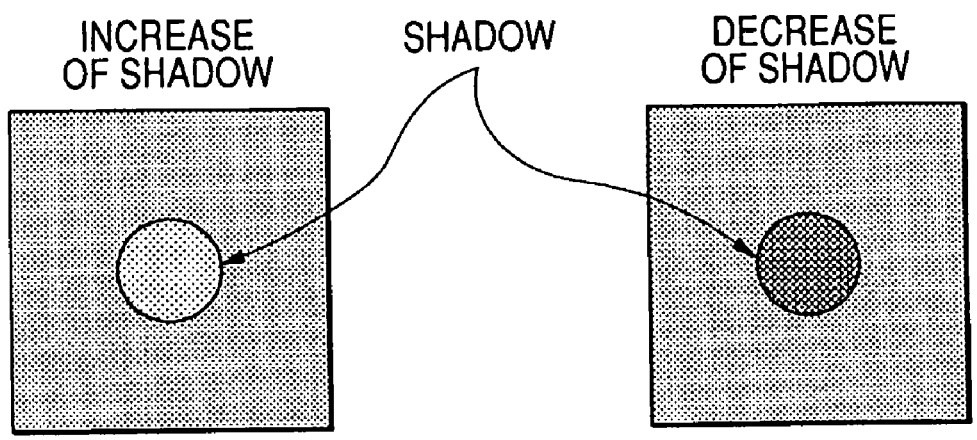
FIGS. 8A and 8B are schematic diagrams showing an example of shadow extraction on the difference image.
Figure 8B:
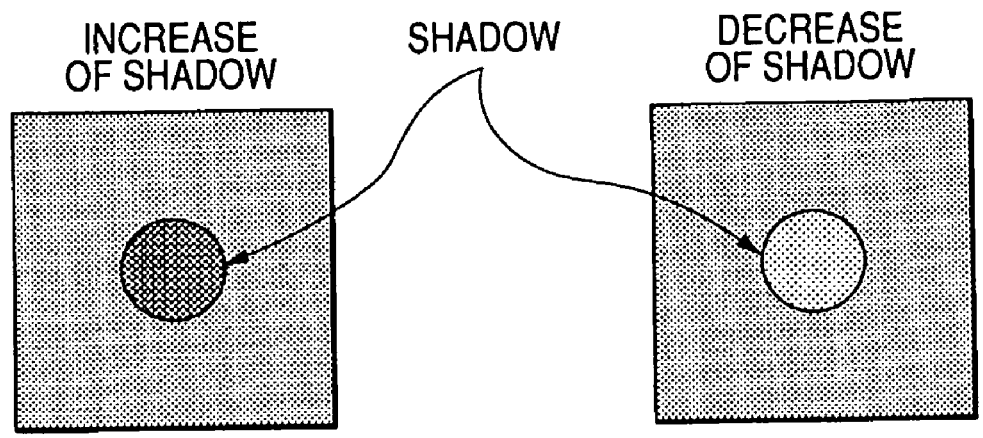

For example, in a case of displaying the difference signal based on a gray scale, the difference signals respectively shown in FIGS. 7A and 7B are displayed as the black region as shown in FIG. 8A when the shadow decreases. Meanwhile, the difference signals are displayed as the white region as shown in FIG. 8B when the shadow increases. For this reason, even if the temporal relation is different between the standard and comparison images, it is possible to maintain quite the same relation. Incidentally, it should be noted that the relation between the increase/decrease of the shadow and the representation on the difference image is not limited to this. That is, for example, the gradation characteristics on the display may be inverted and displayed as shown in FIG. 8B.

{Modification 2}

In the above, the case where the date and hour of radiography of the reference image is recent as compared with those of the comparison images and the case where the date and hour of radiography of the reference image is earlier than those of the comparison images are explained. Besides, a case where the comparison images are radiographed before and after the date and hour of radiography of the reference image will be explained hereinafter as modification 2 of the first embodiment. In the following, as well as in the first embodiment, modification 2 will be explained with reference to the flow chart shown in FIG. 3.

(Step S110)

FIG. 13A shows the status that the reference image is selected. More specifically, FIG. 5A shows the status that the center line in the displayed list is selected as the reference image. In this connection, the mark "S" indicating that the relevant line is selected as the reference image is displayed on the left side of the selected line.

(Step S120)

As well as in the above, the user selects the comparison image by using the mouse. At that time, the mark "R" indicating that the relevant line is selected as the comparison image is displayed on the left side of each of the selected lines. For example, in FIG. 13B, the four images corresponding to the first to second lines and the fourth to fifth lines are selected as the comparison images. Here, it should be noted that the selected comparison images include the comparison images selected both before and after the reference image is selected.

(Step S130)

The image comparison unit 3 compares the dates and hours of radiography with respect to each pair of the selected reference and comparison images, determines the order of difference in the later-described difference process, and outputs the determined order to the difference processing unit 4.

Here, the order of difference which is determined through the combination of the first embodiment and the above modifications is as shown in FIG. 14A. That is, if the reference image is given as S and the comparison images are given as R1 to R4, the difference processing unit 4 operates to generate the difference images TS1 to TS4 which satisfy the following equations:

$$TS1 = R1 - S \quad (7)$$

$$TS2 = R2 - S \quad (8)$$

$$TS3 = S - R3 \quad (9)$$

$$TS4 = S - R4 \quad (10)$$

In the above processing method, problems should not occur in a case where the shadow of focus uniformly decreases or uniformly increases. However, if chemical therapy is executed in the actual medical treatment, the shadow of focus tends repeatedly to increase and decrease. In such a case, regardless of the temporal relation between the reference image and the comparison image, to subtract the past image from the reference image is easy to understand in the diagnosis. That is, when the date and hour of radiography of the reference image is earlier than the date and hour of radiography of the comparison image, the subtraction in the difference process is executed in the same direction as that in the above modification. On the contrary, when the date and hour of radiography of the reference image is later than the date and hour of radiography of the comparison image, the difference process is executed in the direction opposite to that in the first embodiment. In modification 2, the order of difference which is determined by the image comparison unit 3 is as shown in FIG. 14B. That is, if the reference image is given as S and the comparison images are given as R1 to R4, the difference processing unit 4 operates to generate the difference images TS1 to TS4 which satisfy the following equations:

$$TS1 = S - R1 \quad (11)$$

$$TS2 = S - R2 \quad (12)$$

$$TS3 = S - R3 \quad (13)$$

$$TS4 = S - R4 \quad (14)$$

(Step S140)

As well as the above explanation, the difference processing unit 4 generates and outputs the difference image. The registration process is executed not to deform the reference image but to deform the comparison image so as to conform the location of the comparison image to that of the reference image. Here, it should be noted that each of the deformed comparison images is subtracted from the reference image in the order of difference operation as shown in the above equations (11) to (14) and FIG. 14B, thereby generating the difference image.

Here, since the following steps are the same as those already explained, the explanation thereof will be omitted.

By executing the above process, it is possible effectively to generate the difference images even if there are plural combinations of the images to be compared. In addition, it is always possible to maintain a unique relation between a signal in the difference image and the change that has actually occurred between the images.

Figure 15A:
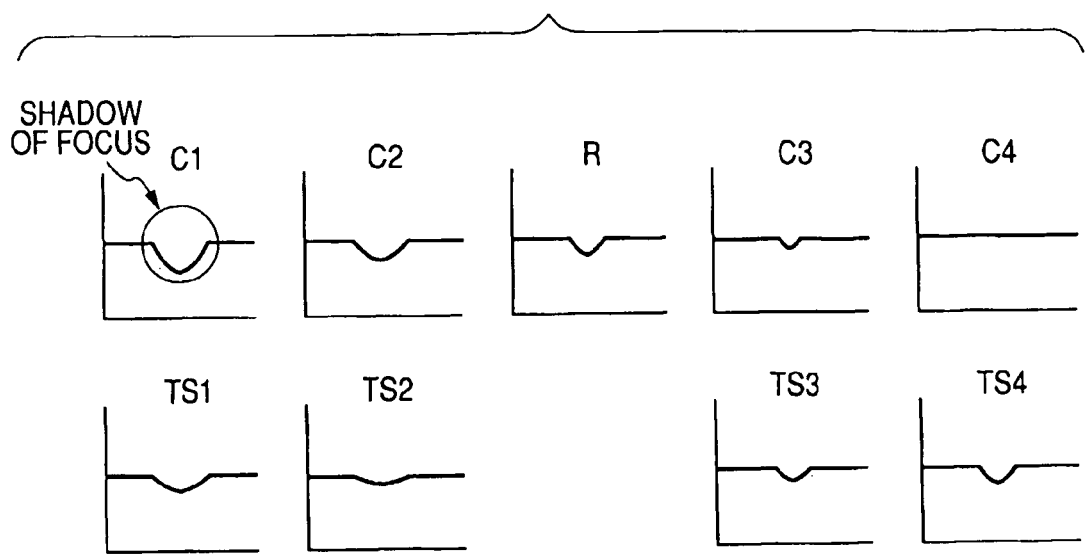
FIGS. 15A and 15B are diagrams for explaining the relation between a change of shadow and the difference signal.
Figure 15B:
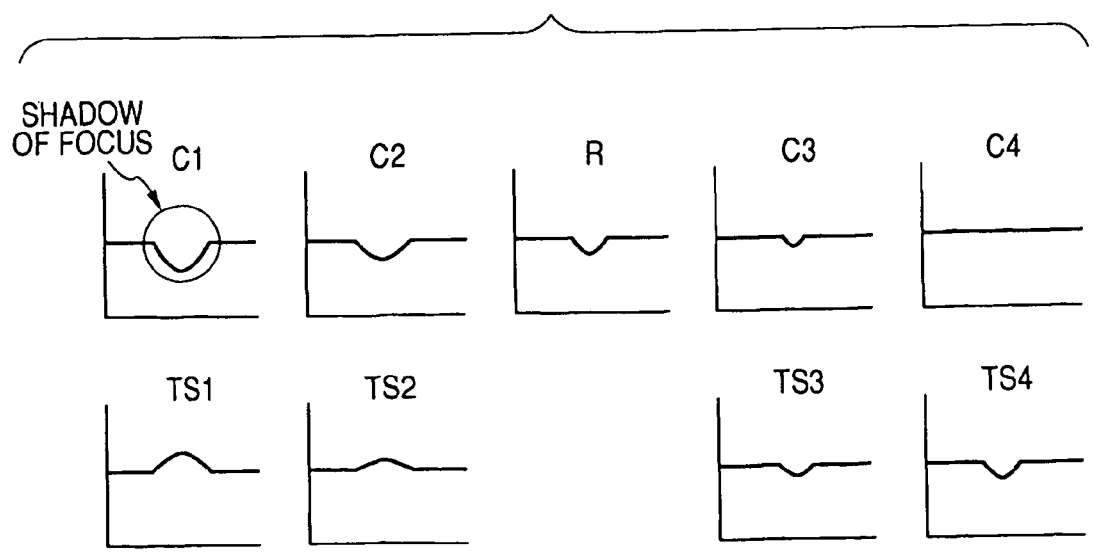

FIGS. 15A and 15B are schematic diagrams which respectively show, as one-dimensional pixel value data, examples of the images and the temporal differences in the modification 2.

First, each of the upper five plots shown in FIG. 15A indicates the pixel value in the vicinity of the shadow of focus in each image, and these five plots are corresponding to FIGS. 13A and 13B and FIG. 14A. More specifically, the shadow of focus becomes small gradually from the comparison image R1 to the comparison image R4, and then the shadow of focus completely disappears in the reference image S which was most recently radiographed. Here, if the difference images TS1, TS2 and TS4 are generated as shown by FIG. 14A and equations (7) to (10), the magnitude of the difference signal becomes small according as it comes close to the magnitude of the shadow of focus in the reference image. However, the condition of the change of the shadow is plotted as the difference signal having the wholly low pixel value as opposed to the background portion on which any change does not occur in the difference image.

Meanwhile, with respect to the example shown in FIGS. 13A and 13B, the difference signal is acquired as shown in FIG. 15B. That is, in the comparison image of which the shadow of focus is smaller than that of the reference image, the difference signal corresponding to the shadow of focus has the low value with respect to the background on which no change occurs. Meanwhile, in the comparison image of which the shadow of focus is larger than that of the reference image, the difference signal corresponding to the shadow of focus has the high value with respect to the background on which any change does not occur. Incidentally, in a case of displaying the above difference signal, for example, the signal value corresponding to the background portion is set to be equivalent to the median of the brightness level capable of being displayed by a display device such as a CRT monitor or the like, and the display itself is executed by using, e.g., a gray region.

For this reason, the difference images generated by equations (4) to (14) in modifications 1 and 2 can be displayed by only executing a black/white reversal process on the difference images generated by equations (1) to (3). In this connection, it is also possible first to generate the difference images all in the same direction, and then execute the black/white reversal process according to the temporal relation of the reference and comparison images.

Moreover, in the different process of the present invention, the comparison image is always deformed for the registration irrespective of the temporal relation of the reference and comparison images. Therefore, in a case of interpreting the difference image generated from a series of comparison images, it is possible always to generate the difference image based on the orientation (posture) of the subject in one reference image, whereby it is possible to easily interpret the generated difference image.

Figure 12A:
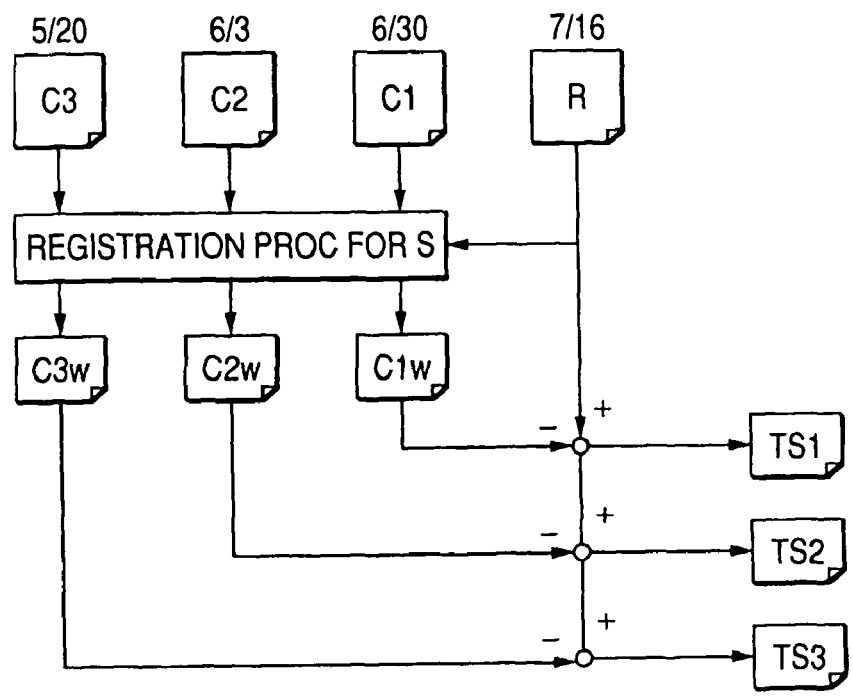
FIGS. 12A and 12B are diagrams for explaining registration of images, according to the present invention.
Figure 12B:
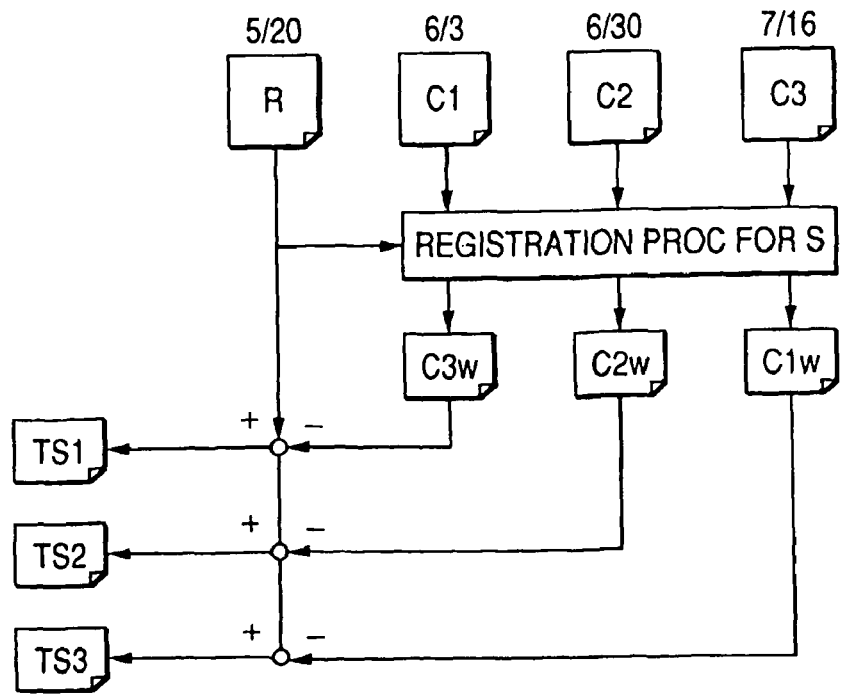

FIGS. 12A and 12B are diagrams showing examples of the above situation. Here, it should be noted that FIG. 12A corresponds to FIGS. 4A and 4B, and FIG. 12B corresponds to FIGS. 5A and 5B.

That is, FIGS. 12A and 12B show the basic of the above difference image process in more detail. More specifically, the deformed images R1w to R3w, all registered with respect to the reference image S, are generated in relation to the comparison images R1 to R3. These deformed images are temporarily generated inside the difference processing unit 4 and are directly used in the difference process.

In FIGS. 12A and 12B, it should be noted that each deformed image has been registered with respect to the reference image S. For this reason, even if the orientation of the subject in each radiographed image differs from others, the orientation of the subject in each of the deformed images R1w to R3w conforms to the reference image S.

In other words, in FIG. 12A, since each of the comparison images R1 to R3 has thus been registered with respect to the reference image S, the orientation of the subject in the difference image is the same as that in the reference image S. Meanwhile, as shown in FIG. 12B, even in the case where the reference image S is radiographed the earliest (i.e., May 20), the orientation of the subject in each difference image is the same as in the reference image S. For these reasons, even where plural difference images are compared with others, it is possible easily to grasp the correspondence between the attended portions, and it is thus easier to perform the diagnosis.

Second Embodiment

In the first embodiment, the reference image and the comparison images are listed on the screen, and a user selects arbitrary images from the displayed list. Otherwise, it is possible to display the images themselves on the screen to enable the user to select the arbitrary images while directly viewing them.

Figure 9:
FIG. 9 is a schematic diagram showing an example of an image selection screen according to the second embodiment of the present invention.

FIG. 9 is a schematic diagram showing an example in which a reduction image is selected by using a mouse to select the reference image or the comparison image.

In FIG. 9, the information indicating the test date and time or the like is displayed next to the displayed relevant reduction image, and, when the reduction image is clicked, the clicked reduction image is set as the reference image.

In any case, the method of arranging the reduction images is not limited to this; that is, various methods are applicable. For example, as disclosed in Japanese Patent Application Laid-Open No. 10-155746 described above, it is possible to arrange a series of time-series images vertically and horizontally in a selectable manner.

Moreover, in a case of selecting the reference image and the comparison images, it is possible not to provide any selection button such as the above buttons B1 and B2. In that case, it is possible to select the target image by using plural buttons attached to the mouse. In addition, in a case of selecting plural comparison images, it is possible to operate using an appropriate combination of mouse and keyboard operations. In that case, for example, the user clicks the mouse as depressing a specific key to select the plural images.

Third Embodiment

In the first and second embodiments, the screen used for selecting the images is independently provided, and the reference image and the comparison images are selected by using this screen. However, the present invention is not limited to this. That is, it is possible to select the target images on the screen typically used for executing image diagnosis.

Figure 10A:
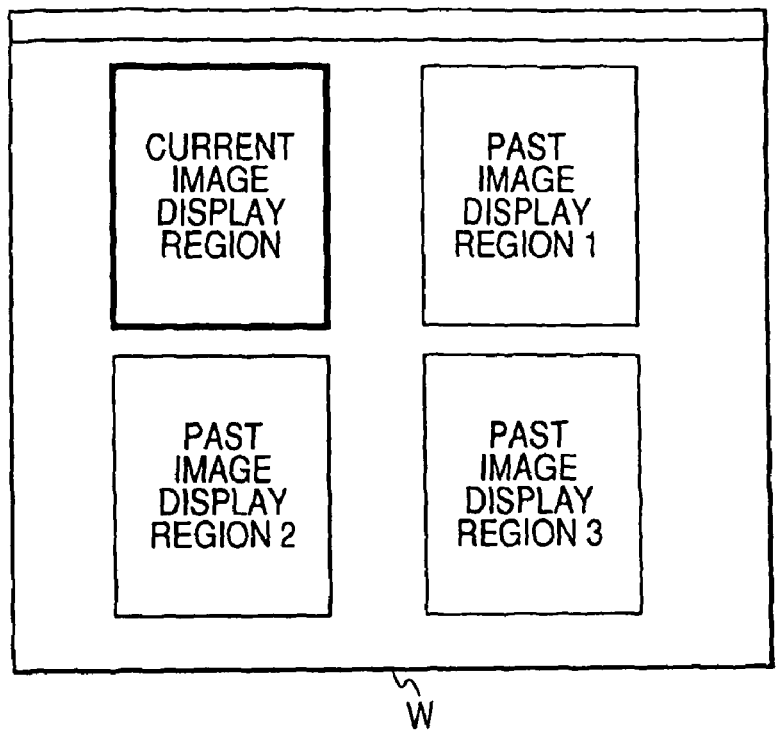
FIGS. 10A and 10B are schematic diagrams showing an example of an image selection screen according to the third embodiment of the present invention.
Figure 10B:
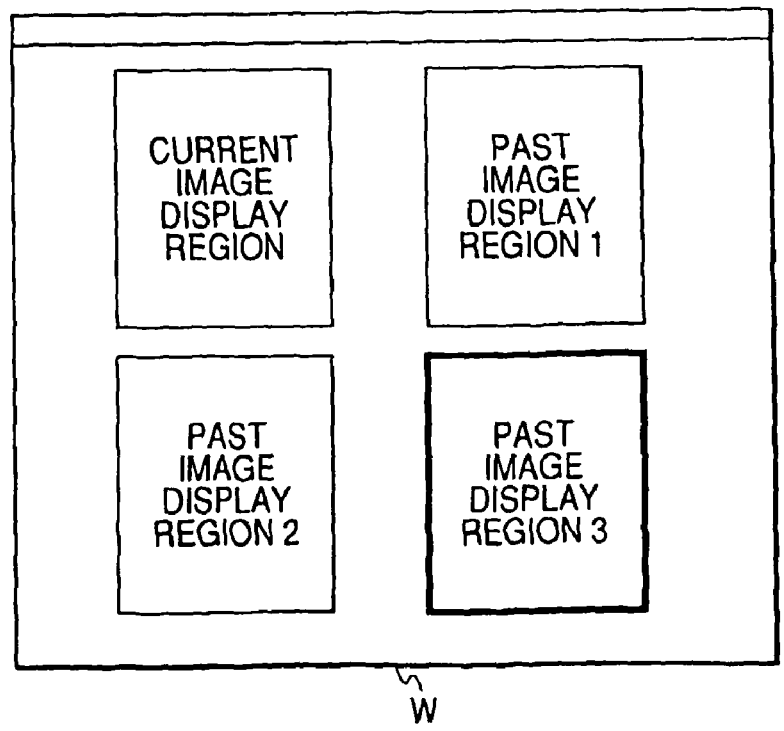

FIGS. 10A and 10B are schematic diagrams showing an example of image display on the image display unit 7 in the diagnosis.

In FIG. 10A, there are four image display regions in a window W, and the images of an identical patient are displayed sequentially from the upper left region to the lower right region in order of recent (latest) radiography time. Here, if the region which is clicked and of which the frame is thus emphatically displayed is set as the reference image and other regions are set as the comparison images, it is possible appropriately to select the images according to their display locations on the screen.

That is, when the latest (current) image is set as the reference image and the remaining three images are set as the comparison images as shown in FIG. 6A, it is only necessary to select the upper left region as the reference image region as shown in FIG. 10A. Meanwhile, when the earliest (most past) image is set as the reference image as shown in FIG. 6B, if the display region of the most-past image is selected from the display image regions, it is possible thereby to select the image of the selected region as the reference image.

As explained above, according to the present embodiment, in case of generating the temporal difference image based on the plural combinations of the images, even if the method of combining the images to be compared and interpreted is changed, it is possible consistently to extract the change of the shadow of focus. In addition, it is possible effectively to generate the difference image with the orientation of the subject maintained, and thus, it is possible to achieve image processing which can execute the effective difference process in progress observation.

Other Embodiments to which the Present Invention is Applied

It should be noted that the image comparison unit 3, the difference processing unit 4, the image designation unit 5 and the display control unit 6 which are the main constituents of the image processing device according to the above embodiments, and the respective steps (e.g., steps S110 to S160 shown in FIG. 3) of the image processing methods according to the above embodiments, can be achieved by operating programs stored in the RAM, the ROM or the like of a computer. In this connection, the relevant programs and a computer-readable storage medium which stores therein the relevant programs are included in the concept of the present invention.

Moreover, the relevant programs are supplied to the computer through the storage medium such as, e.g., a CD-ROM or through various transmission media. As the storage medium for recording the relevant programs, for example, a flexible disk, a hard disk, a magnetic tape, a magnetooptical disk, a nonvolatile memory card or the like can be used as well as the CR-ROM. In addition, as the transmission media for supplying the relevant programs, communication media (a wired line such as an optical fiber, a wireless line, etc.) in a computer network (a LAN (local area network), a WAN (wide area network) such as the Internet, a wireless communication network, etc.) system for transmitting program information as carrier waves to supply the relevant programs can be used.

Moreover, the present invention includes not only a case where the functions of the above embodiments are achieved when the computer executes the supplied programs, but also a case where an OS (operating system) or the OS in association with other application software functioning on the computer achieves the functions of the above embodiments. In addition, the present invention also includes a case where a function expansion board inserted in the computer or a function expansion unit connected to the computer executes a part or all of the actual processes based on the supplied programs, the functions of the above embodiments are thus achieved. In other words, in such cases, the relevant programs are included in the present invention.

In the main constitution of the image processing device, each unit can be implemented as the logical constituent element in one program or an independent library. The relevant program is stored in such a hard disk HD as shown in FIG. 2. Then, the storage program is read in response to a not-shown user input or another indication input, the read program is uncompressed on the RAM, and the program is sequentially executed by the CPU, thereby achieving the functions of the above embodiments. Alternatively, the program may be stored in the ROM or a file server FS connected to the device through a network N.

Moreover, some or all of the above constituent elements can be implemented using such hardware as an accelerator ACC shown in FIG. 2. More specifically, it is possible to connect the accelerator ACC to the bus BUS as the hardware including the difference processing unit 4 and other functions, whereby it is also possible to cause the CPU to execute the whole control of the relevant hardware.

The invention claimed is:

1. An image processing device comprising:
   a storage unit adapted to store plural images;
   an image designation unit adapted to designate a reference image and comparison images from among the plural images stored by said storage unit;
   a comparison unit adapted to acquire radiography date and time information of the designated reference image and the designated comparison images, and compare the radiography date and time information of the reference image with the radiography date and time information of each of the comparison images;
   a determination unit adapted to determine, based on each of the comparison results provided by said comparison unit, whether to subtract the comparison image from the reference image or subtract the reference image from the comparison image; and
   a difference image generation unit adapted to generate the temporal difference image from the reference image and each of the comparison images by using the determination, corresponding to the each of the comparison images, determined by said determination unit.

2. An image processing device according to claim 1, wherein said difference image generation unit deforms each of the comparison images on the basis of the reference image designated by said image designation unit, and generates the temporal difference image from the reference image and the deformed comparison image.

3. An image processing device according to claim 1, wherein said image designation unit can display a list of the images stored by said image storage unit, and selects the reference image and the comparison images from the displayed list of the images.

4. An image processing device according to claim 1, wherein said image designation unit can display reduction images acquired by reducing the images stored by said storage unit, and selects the reference image and the comparison images based on an indication input with respect to the displayed reduction images.

5. An image processing device according to claim 1, wherein said image designation unit can display the images stored by said storage unit in predetermined order based on the radiography date and time information, and selects the reference image and the comparison images based on an indication input with respect to the displayed images.

6. An image processing device according to claim 1, wherein said difference image generation unit determines, based on the comparison result provided by said comparison unit, to subtract the image whose radiography date and time information indicates a more recent date and time from the image whose radiography date and time information indicates a less recent date and time.

7. An image processing method comprising:
   an image designation step of designating a reference image and comparison images from among plural images stored in a storage unit;
   a comparison step of acquiring radiography date and time information of the designated reference image and the designated comparison image, and comparing the radiography date and time information of the reference image with the radiography date and time information of each of the comparison images;
   a determination step of determining, based on each of the comparison results obtained in said comparison step, whether to subtract the comparison image from the reference image or subtract the reference image from the comparison image; and
   a difference image generation step of generating the temporal difference image from the reference image and each of the comparison images by using the determination, corresponding to the each of the comparison images, determined in said determination step.

8. An image processing method according to claim 7, wherein said difference image generation step includes deforming each of the comparison images on the basis of the reference image designated in said image designation step, and generating the temporal difference image from the reference image and the deformed comparison image.

9. An image processing method according to claim 7, wherein said image designation step includes displaying a list of the stored images, and selecting the reference image and the comparison images from the displayed list of the images.

10. An image processing method according to claim 7, wherein said image designation step enables the display of reduction images acquired by reducing the stored images, and includes selecting the reference image and the comparison images based on an indication input with respect to the displayed reduction images.

11. An image processing method according to claim 7, wherein said image designation step enables the display of the stored images in a predetermined order based on the radiography date and time information, and includes selecting the reference image and the comparison images based on an indication input with respect to the displayed images.

12. An image processing method according to claim 7, wherein said difference image generation step includes determining, based on the comparison result obtained in said comparison step, to subtract the image whose radiography date and time information indicates a more recent date and time from the image whose radiography date and time information indicates a less recent date and time.

13. A non-transitory computer-readable storage medium which stores a control program for causing a computer to perform a method including:
   an image designation step of designating a reference image and comparison images from among plural images stored in a storage unit;

a comparison step of acquiring radiography date and time information of the designated reference image and the designated comparison image, and comparing the radiography date and time information of the reference image with the radiography date and time information of each of the comparison images;

a determination step of determining based on each of the comparison results obtained in said comparison step, whether to subtract the comparison image from the reference image or subtract the reference image from the comparison image;

and a difference image generation step of generating the temporal difference image from the reference image and each of the comparison images by using the determination, corresponding to the each of the comparison images, determined in said determination step.

14. A non-transitory computer-readable storage medium according to claim 13, wherein said difference image generation step includes deforming each of the comparison images on the basis of the reference image designated in said image designation step, and generating the temporal difference image from the reference image and the deformed comparison image.

15. A non-transitory computer-readable storage medium according to claim 13 wherein said image designation step includes displaying a list of the stored images and selecting the reference image and the comparison images from the displayed list of the images.

16. A non-transitory computer-readable storage medium according to claim 13 wherein said image, designation step enables the display of the stored images in a predetermined order based on the radiography date and time information, and includes selecting the reference image and the comparison images based on an indication input with respect to the displayed images.

17. A non-transitory computer-readable storage medium according to claim 13, wherein said difference image generation step includes determining, based on the comparison result obtained in said comparison step, to subtract the image whose radiography date and time information indicates more recent date and time from the image whose radiography date and time information indicates a less recent date and time.

* * * * *